United States Patent [19]

Goswami et al.

[11] Patent Number: 5,302,350
[45] Date of Patent: Apr. 12, 1994

[54] SPECIFIC AND REVERSIBLE CARBON MONOXIDE SENSOR

[75] Inventors: Kisholoy Goswami; Devinder P. S. Saini; Stanley M. Klainer, all of Henderson; Chuka H. Ejiofor, Las Vegas, all of Nev.

[73] Assignee: FCI - FiberChem, Inc., Las Vegas, Nev.

[21] Appl. No.: 9,066

[22] Filed: Jan. 26, 1993

[51] Int. Cl.$^5$ .................... G01N 31/00; G01N 33/00
[52] U.S. Cl. ........................ 422/86; 422/83; 436/134
[58] Field of Search ................. 422/83, 86, 98; 436/134, 169, 164; 502/400, 406

[56] References Cited

U.S. PATENT DOCUMENTS

| | | | |
|---|---|---|---|
| 2,487,077 | 11/1949 | Shepherd | 436/134 |
| 4,043,934 | 8/1977 | Shuler et al. | 436/134 X |
| 4,224,280 | 9/1980 | Takahama et al. | 422/98 |
| 4,441,981 | 4/1984 | Okamoto et al. | 204/426 |
| 4,482,635 | 11/1984 | Herskovitz et al. | 436/134 |
| 5,063,164 | 11/1991 | Goldstein | 436/169 |

*Primary Examiner*—James C. Housel
*Assistant Examiner*—Robert Carpenter
*Attorney, Agent, or Firm*—Henry P. Sartorio

[57] ABSTRACT

A molybdenum salt-palladium salt solution for CO detection is made reversible by addition of ferric ion. The system is made more CO specific by adding an interference control salt which forms white or colorless precipitates with interfering species. The operational and shelf life are extended by a mixture of counterions; the acetate counterion is particularly useful.

18 Claims, 1 Drawing Sheet

SPECIFIC AND REVERSIBLE CARBON MONOXIDE SENSOR

BACKGROUND OF THE INVENTION

The invention relates generally to chemical sensors and more particularly to carbon monoxide sensors.

The reaction of Carbon Monoxide (CO) with a variety of molybdenum compounds is reported as early as 1910 [C. Zenghelis, Z. Anal. Chem, 40, 429, (1910)] and the literature is reviewed in 1935 by J. Schmidt, "Das Kohlenoxyd", Akad. Verlag, Leipzig, p 186, (1935). It is further presented in "Spot Tests in Inorganic Analysis" by F. Feigel in 1937. [F. Feigel, V. Anger, R. Oesper, "Spot Tests in Inorganic Analysis", Elsevier Publishing Company, New York, p. 168 (1972)].

In this relevant literature, three (3) basic equations are pointed out:

$$Mo^{+6} + CO \rightarrow Mo^{+3} + CO_2 \quad (1)$$

$$Pd^{+2} + CO + H_2O \rightarrow Pd^0 + CO_2 + 2H^+ \quad (2)$$

$$Pd^0 + Mo^{+6} \rightarrow Pd^{+2} + Mo^{+3} \quad (3)$$

The reaction in Equation (1) is very slow and, therefore, a catalyst ($Pd^{+2}$) is used. The $Pd^{+2}$, even in very small quantities, adsorbs and simultaneously gets reduced by CO as shown in Equation (2). $Pd^0$, in turn, enters into the reaction, Equation (3), producing molybdenum blue. Thus, a slightly yellow solution is changed to a blue color with the intensity of the blue color being directly related to CO exposure. As presented in Equations (1), (2) and (3), the reaction is not reversible and, therefore, has limited application in sensor technology.

To make the system reversible, therefore, there must be a secondary

The invention relates generally to chemical sensors and more reaction which converts $Mo^{+3}$ back to $Mo^{+6}$, i.e., an oxidizer must be present.

The question of the reversible CO sensor is addressed by M. K. Goldstein in U.S. Pat. No. 5,063,164. That patent suggests several possible chemical recipes for this type of sensor, but does not address the criteria or requirements for a successful reversible sensor; nor does it address the chemistry or mechanisms to make the CO sensor completely specific.

Goldstein shows a solid state CO sensor having five components: (1) palladium salt, (2) molybdenum and/or tungsten salt or acid salt, (3) copper salt, (4) cyclodextrin molecular encapsulant which encapsulates at least one but not all of the other components, and (5) chloride salt, all impregnated into a substrate.

SUMMARY OF THE INVENTION

Accordingly, it is an object of the invention to provide an improved CO sensor.

It is also an object of the invention to provide a reversible CO sensor.

It is another object of the invention to provide a specific CO sensor which eliminates interferences.

It is a further object of the invention to provide a CO sensor with extended lifetime.

The invention is a reversible CO sensor formed of an aqueous solution of (1) tungsten and molybdenum salts or acid salts, (2) palladium salt, (3) iron salt. The iron salt provides ferric ion as a reversing agent. The solution further can include a sodium salt which forms a white or colorless sulfide to eliminate interferences and increase specificity. The invention further includes a long-life CO sensor based on palladium with mixed counterions. The CO sensor is formed of an aqueous solution of (1) tungsten and molybdenum salts or acid salts, (2) palladium salt, (3) Pd(II) redox controlling counterion producing salt and (4) $Fe^{+3}$ ion as the reversing agent.

DETAILED DESCRIPTION OF THE PREFERRED EMBODIMENTS

Figure 1:
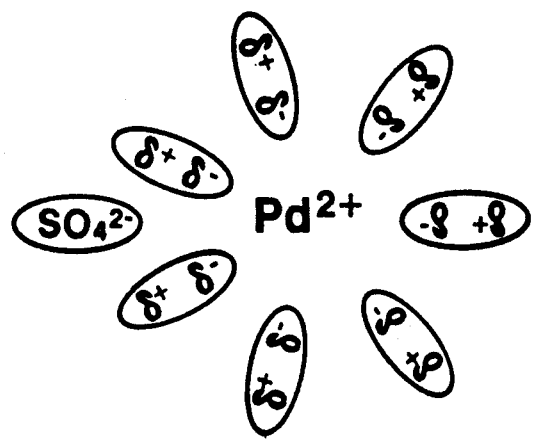
FIG. 1 is a diagram of a Pd(II) ion surrounded by water dipoles.

The choice of a reversing agent depends on its ability to produce the desired reactions only, and nothing more. The first requisite is that the $Mo^{+3}$ formed with the reaction of $Pd^{+2}$, CO and $Mo^{+6}$ goes back to $Mo^{+6}$ and no other valence states of the Mo. This requires a reversing compound whose redox potential closely matches that of $Mo^{+3}$ going to $Mo^{+6}$ so that the reaction proceeds spontaneously in the thermodynamic sense. The second requirement is that the selected oxidizing agent, when used, regenerates itself and not a series of compounds of various chemical formula and valence states. Based on these criteria, ferric ion is selected (irrespective of the counter ion) as the reversing agent in the formulation of a CO sensing chemistry. The reverse reaction proceeds as follows:

$$Mo^{+3} + 3Fe^{+3} \rightarrow Mo^{+6} + 3Fe^{+2} \quad (4)$$

Eventually, by air oxidation $Fe^{+2}$ returns to $Fe^{+3}$ to be available for reuse.

The amount of ferric ion (such as ferric chloride) used strictly depends on the dynamic range of concentrations of CO to be detected and the desired time delay for reversibility. In fact, if time is not a criterion, the reliance on oxygen in the air to cause the reversibility is perfectly acceptable.

The CO sensor chemistry is thus a solution of (1) tungsten or molybdenum salts or acid salts which provides the $W^{+6}$ or $Mo^{+6}$ ion, (2) palladium salt which provides the $Pd^{+2}$ ion, and (3) iron (ferric) salt which provides the $Fe^{+3}$ ion. The solution is typically aqueous, but other solvents might be used. The tungsten acid/salt may be selected from tungstosilicic acid and salts, thereof, tungsten trioxide, heteropolyacids of tungsten, ammonium tungstate and alkali metal, or alkaline earth metal salts of the tungstate ion. The molybdenum acid/salt may be selected from molybdosilicic acid and salts thereof, molybdenum trioxide, heteropolyacids of molybdenum, ammonium molybdate, and alkali metal or alkaline earth metal salts of the molybdate anion. The palladium salt may be selected from palladium sulfate, palladium sulfite, palladium pyrosulfite, palladium chloride, palladium bromide, palladium iodide, palladium perchlorate, $CaPdCl_4$, $Na_2PdCl_4$, $K_2PdCl_4$. The iron (ferric) salt may be selected from ferric chloride, ferric sulfate, ferric bromide, ferric iodide, and ferric perchlorate. All the salts must be soluble.

In operation, the $Mo^{+6}$ is reduced to $Mo^{+3}$ by the CO in the presence of the $Pd^{+2}$ catalyst. The $Fe^{+3}$ then oxidizes the $Mo^{+3}$ back to $Mo^{+6}$.

For the detection of CO between 0 and 500 ppm, a typical chemical system consists of:

Palladium Sulfate (0.04 wt. %)
Molybdosilicic Acid (0.2 wt. %)
Ferric Chloride (0.04 wt. %)

in aqueous solution. This composition is modified for other dynamic ranges.

The second part of the requirement for a CO sensor is that it be specific. All existent CO sensors including the one defined in U.S. Pat. No. 5,063,164 suffer from a variety of interferences of which hydrogen sulfide is most common. For example, palladium sulfide, molybdenum sulfide and copper sulfide (which would be formed in U.S. Pat. No. 5,063,164) are all black/brown which prohibits measurement of the yellow to blue color change when $Mo^{+6}$ is reduced to $Mo^{+3}$. Iron sulfide, which is yellow/green can also cause some problems. The solution, therefore, is to add a fourth component to the system which not only preferentially forms a sulfide, but a white or colorless one which will not interfere with the CO measurement. To accomplish this, sodium chloride (2 wt. %) is incorporated into the system.

The four (4) component chemical system was extensively tested with a UV/VIS spectrophotometer. The following table shows the results of these tests. This formulation for a CO sensor indicates no response to the key Occupational Safety and Health Administration (OSHA) interferences.

| INTERFERENCE LEVEL | | RESPONSE | OSHA LEVEL |
| --- | --- | --- | --- |
| Propane | (1000 ppm) | 0 | 1000 ppm |
| $NO_2$ | (30 ppm) | 0 | 3 ppm |
| Butane | (800 ppm) | 0 | 800 ppm |
| $SO_2$ | (10 ppm) | 0 | 2 ppm |
| $N_2O$ | (100 ppm) | 0 | |
| $H_2S$ | (50 ppm) | 0 | 10 ppm |
| $CO_2$ | (100%) | 0 | 10000 ppm |
| Methane | (100%) | 0 | 1000 ppm |

Other salts can also be used to eliminate interferences and enhance specificity by producing white or colorless precipitates with the interfering species. These salts may be selected from chlorides and perchlorates of sodium, lithium, potassium, calcium, magnesium, aluminum, platinum, cobalt, etc.

Extending the shelf life and operational life of the CO sensor is very important. Doing so is difficult, and involves modification of the redox properties of the catalyst. This was achieved in the following way:

The catalyst is Palladium(II). When common salts of palladium ($PdSO_4$, $PdCl_2$, etc.) are dissolved in water, Pd(II) exists in the solvated form, as shown in FIG. 1. Water molecules form dipoles ($\delta^- - \delta^+$) which surround the Pd (II) ion. The sulfate counterion is also present. The counterions are also similarly solvated.

In the aquo form, Pd(II) is energetically very prone to reduction. When $Pd^{+2}$ is surrounded by neutral molecules like water, ethanol, ethylene glycol, glycerol, and molecules having reducing functional groups, the operational and shelf life of the sensor chemistry are diminished drastically because of reduction without CO. Similar results occur with counterions like $SO_4^{-2}$, $Cl^-$, $PO_4^{-3}$, $HPO_4^{-2}$, etc. Because the species surrounding the $Pd^{+2}$ determines its redox properties, the properties of $Pd^{+2}$ can be controlled by carefully selecting its counterions.

Figure 2:
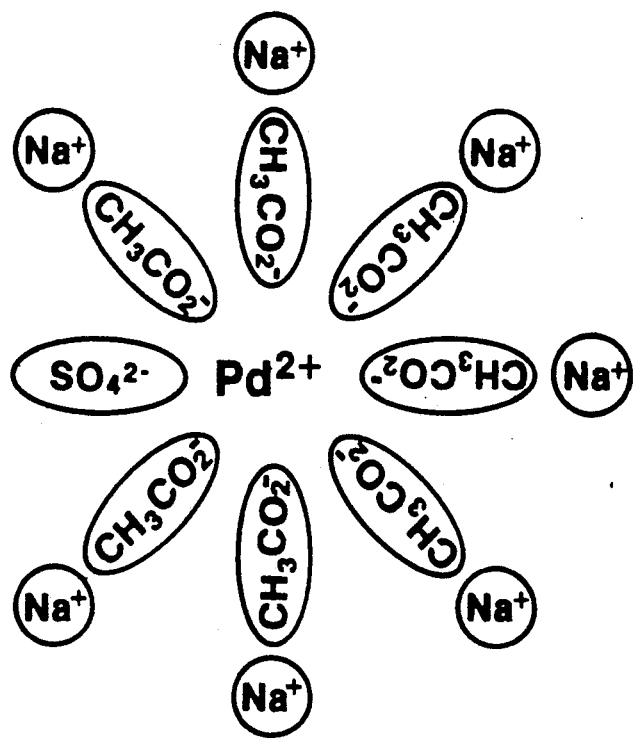
FIG. 2 is a diagram of a Pd(II) ion surrounded by sulfate and acetate counterions.

When neat CO is passed through a solution of $PdSO_4$ in pure water, the solution turns black immediately. However, when $PdSO_4$ is dissolved in sodium acetate saturated water, it takes fifteen times longer to get dark. The acetate ions ($CH_3CO_2^-$) now surround the Pd(II) ion as shown in FIG. 2. The sulfate counterion is also present. Thus, the presence of acetate counterion greatly influences the redox properties of $Pd^{+2}$. This difference between sulfate and acetate counterions is used to extend lifetime.

The invention includes a CO sensing chemistry based on palladium with mixed counterions. By carefully adjusting the proportion of acetate and sulfate, or acetate and chloride counterions, the redox properties of $Pd^{+2}$ are modulated; thereby prolonging the shelf life and operational life of the sensor.

Thus, the invention includes the addition of suitable counterions to the molybdenum/palladium combination. Ferric ion is added for reversibility and sodium salt for specificity as previously described. However, the bicounterion concept is applied to the palladium catalyst to achieve prolonged shelf life and operational life.

The counterion can be provided by the following: sodium acetate, potassium acetate, ammonium acetate, etc. The amount of counterion to be added is typically in the range of ten times the molar concentration of palladium. To accomplish this, sodium acetate (0.16 wt. %) is incorporated into the system.

Changes and modifications in the specifically described embodiments may be carried out without departing from the scope of the invention which is intended to be limited only by the scope of the appended claims.

We claim:

1. A CO sensor comprising, in solution:
    a source of $Mo^{+6}$ or $W^{+6}$ ions;
    a source of $Pd^{+2}$ ions;
    a source of $Fe^{+3}$ ions;
    a source of $CH_3CO_2^-$ counterions in an amount sufficient to substantially prevent the $Pd^{+2}$ ions from being reduced to $Pd^0$ by other ions in the absence of CO.

2. The CO sensor of claim 1 wherein
    the source of $Mo^{+6}$ or $W^{+6}$ ions is a molybdenum salt or molybdenum acid salt;
    the source of $Pd^{+2}$ ions is a palladium salt;
    the source $Fe^{+3}$ ions is an iron salt;
    the source of $CH_3CO_2^-$ counterions is an acetate.

3. The CO sensor of claim 2 wherein
    the molybdenum salt or molybdenum acid salt is selected from the group consisting of molybdosilicic acid and salts thereof, molybdenum trioxide, heteropolyacids of molybdenum, ammonium molybdate, and alkali metal or alkaline earth metal salts of the molybdate anion;
    the palladium salt is selected from the group consisting of palladium sulfate, palladium sulfite, palladium pyrosulfite, palladium chloride, palladium bromide, palladium iodide, palladium perchlorate, $CaPdCl_4$, $Na_2PdCl_4$, $K_2PdCl_4$;
    the iron salt is selected from the group consisting of ferric chloride, ferric sulfate, ferric bromide, ferric iodide, and ferric perchlorate;

the acetate is selected from the group consisting of sodium acetate, potassium acetate and ammonium acetate.

4. The CO sensor of claim 3 wherein the molybdenum salt or molybdenum acid salt is molybdosilicic acid, the palladium salt is palladium sulfate, the iron salt is ferric chloride and the acetate is sodium acetate.

5. The CO sensor of claim 1 wherein
the source of $Mo^{+6}$ or $W^{+6}$ ions is a tungsten salt or tungsten acid salt;
the source of $Pd^{+2}$ ions is a palladium salt;
the source of $Fe^{+3}$ ions is an iron salt;
the source of $CH_3CO_2^-$ counterions is an acetate.

6. The CO sensor of claim 5 wherein the tungsten salt or tungsten acid salt is selected from the group consisting of tungstosilicic acid and salts thereof, tungsten trioxide, heteropolyacids of tungsten, ammonium tungstate, and alkali metal or alkaline earth metal salts of the tungstate ion;
the palladium salt is selected from the group consisting of palladium sulfate, palladium sulfite, palladium pyrosulfite, palladium chloride, palladium bromide, palladium iodide, palladium perchlorate, $CaPdCl_4$, $Na_2PdCl_4$, $K_2PdCl_4$;
the iron salt is selected from the group consisting of ferric chloride, ferric sulfate, ferric bromide, ferric iodide, and ferric perchlorate;
the acetate is selected from the group consisting of sodium acetate, potassium acetate and ammonium acetate.

7. The CO sensor of claim 6 wherein the tungsten salt or tungsten acid salt is tungstosilicic acid, the palladium salt is palladium sulfate, the iron salt is ferric chloride and the acetate is sodium acetate.

8. The CO sensor of claim 1 further comprising a source of ions which form white or colorless precipitates with sulfide interfering species.

9. The CO sensor of claim 8 where the source of ions which form white or colorless sulfides is a source of $Na^+$ ions.

10. The CO sensor of claim 4 further comprising sodium chloride.

11. The CO sensor of claim 7 further comprising sodium chloride.

12. The CO sensor of claim 1 wherein the molar ratio of $CH_3CO_2^-$ counterions to $Pd^{+2}$ ions is about 10.

13. A CO sensor comprising, in solution:
a source of $Mo^{+6}$ or $W^{+6}$ ions;
a source of $Fe^{+3}$ ions;
a source of $Pd^{+2}$ ions and first counterions;
a source of second counterions to the $Pd^{+2}$ ions which substantially prevent the $Pd^{+2}$ ions from being reduced to $Pd^0$ by the first counterions and other counterions in the solution;
wherein the first counterions are sulfate or other reducing ions and the second counterions are acetate counterions.

14. The CO sensor of claim 13 wherein the molar ratio of second counterions to $Pd^{+2}$ ions is about 10.

15. The CO sensor of claim 13 wherein the source of $Mo^{+6}$ is a molybdenum salt or molybdenum acid salt, the source of $W^{+6}$ is a tungsten salt or tungsten acid salt, the source of $Pd^{+2}$ ions and first counterions is a palladium salt and the source of second counterions is an acetate.

16. The CO sensor of claim 15 wherein the acetate is sodium acetate.

17. The CO sensor of claim 13 further comprising a source of $Na^+$ ions.

18. A CO sensor comprising, in solution:
molybdosilicic acid (0.2 wt. %);
palladium sulfate (0.04 wt. %);
ferric chloride (0.04 wt. %);
sodium chloride (2.0 wt. %);
sodium acetate 0.16 wt. %).

* * * * *